United States Patent

Nagase et al.

[11] 3,970,700
[45] July 20, 1976

[54] RACEMIZATION OF OPTICALLY ACTIVE AMINES

[75] Inventors: Tsuneyuki Nagase, Takatsuk; Gohu Suzukamo, Ibaraki; Yoshio Suzuki, Itami, all of Japan

[73] Assignee: Sumitomo Chemical Company, Limited, Japan

[22] Filed: Sept. 6, 1974

[21] Appl. No.: 503,691

[30] Foreign Application Priority Data

Sept. 7, 1973 Japan.............................. 48-101418
Sept. 7, 1973 Japan.............................. 48-101419
Sept. 7, 1973 Japan.............................. 48-101420

[52] U.S. Cl..................... 260/570.8 R; 260/471 A; 260/482 R; 260/570.5 R
[51] Int. Cl.²....................................... C07C 20/00
[58] Field of Search.......... 260/471 A, 570.8, 482 R

[56] References Cited
UNITED STATES PATENTS
3,168,566 2/1965 Loter et al. ................. 260/570.8 R Primary Examiner—Richard L. Raymond
Attorney, Agent, or Firm—Stewart and Kolasch, Ltd.

[57] ABSTRACT

A method for racemization of optically active amines which comprises contacting an optically active amine of the formula:

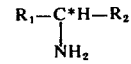

wherein C* is an asymmetric carbon atom, $R_1$ is alkyl, aralkyl or aryl and $R_2$ is aryl or alkoxycarbonyl, the aryl or aralkyl moiety bearing optionally one or more alkyl or alkoxy groups on the aromatic ring, provided that $R_1$ and $R_2$ are always different from each other, with an alkali metal catalyst selected from the group consisting of (1) an alkali metal deposited on a solid carrier, (2) an alkali metal dispersed in a liquid medium and (3) an alkali metal alloy at a temperature of from −10° to 50°C until a sufficient amount of the optically active amine is recemized.

9 Claims, No Drawings

RACEMIZATION OF OPTICALLY ACTIVE AMINES

The present invention relates to a method for racemization of optically active amines.

The optically active amines which can be racemized by the present invention are representable by the formula:

wherein C* is an asymmetric carbon atom, $R_1$ is alkyl, aralkyl or aryl and $R_2$ is aryl or alkoxycarbonyl, the aryl or aralkyl moiety bearing optionally one or more alkyl or alkoxy groups on the aromatic ring, provided that $R_1$ and $R_2$ are always different from each other.

Optically active amines [I] are useful as industrial chemicals, agricultural chemicals and the like. They are also useful as intermediates in the production of useful chemical substances. Further, they are useful as resolution agents for the preparation of (+)-trans-chrysanthemic acid [U.S. Pat. No. 3,739,019].

In general, these optically active amines [I] are industrially produced in the form of racemic mixtures, which are then subjected to resolution. After separation of the optical antipodes which are useful, the remaining undesirable antipodes are subjected to racemization and resolution, whereby the optical antipodes which are useful are additionally obtained. Thus, racemization is one of the valuable methods for production of the optically active amines [I].

For achieving such racemization of optically active amines [I], it is known that an optically active amine such as d-α-phenylethylamine, 1-α-phenylethylamine, d-α-(α-naphthyl)ethylamine or 1-α-(α-naphthyl)ethylamine is heated with an alkali metal in an inert atmosphere at temperatures between 60°C and the boiling point of said optically active amine [U.S. Pat. No. 3,168,566]. This known method is disadvantageous in requiring heating at relatively high temperatures and is not satisfactory in the yield of racemization.

As the result of an extensive study on the racemization of optically active amines [I], it has now been surprisingly found that some certain catalysts are quite effective in racemization of said amines and can afford their racemic mixtures in quantitative yields with ease at ambient temperatures.

According to the present invention, the optically active amine [I] is contacted with an alkali metal catalyst selected from the group consisting of (1) an alkali metal deposited on a solid carrier (hereinafter referred to as "Catalyst A"), (2) an alkali metal dispersed in a liquid medium (hereinafter referred to as "Catalyst B") and (3) an alkali metal alloy (hereinafter referred to as "Catalyst C") until a sufficient amount is racemized. The present invention will now be explained more in detail by the following descriptions.

The term "alkali metal catalyst" is intended to mean an alkali metal processed in any form suitable for exertion of the catalytic activity, particularly the catalyst selected from the group consisting of Catalyst A, Catalyst B and Catalyst C. As the alkali metal, there may be used any one belonging to Group I of the periodic table, for instance, lithium, sodium, potassium, rubidium, or alloys thereof.

Catalyst A may be prepared by depositing the alkali metal on a solid carrier such as alumina, silica gel, aluminum silicate, magnesium silicate or activated carbon. The solid carrier is preferred to have a surface area of at least about 25 m² per 1 gram, and a higher surface area is more effective. For preparation of a suitable catalyst, the deposition of the alkali metal on the solid carrier is effected at a temperature higher than the melting point of the alkali metal under the atmosphere of an inert gas such as nitrogen, helium or argon. Particularly when alumina is employed as the solid carrier, a highly active catalyst can be obtained by making the deposition at a temperature of from 200° to 500°C. The amount of the alkali metal to be used is usually from 1 to 30% by weight, favorably from 4 to 20% by weight, based on the weight of the solid carrier. The catalyst of this type is known as a catalyst effective in the isomerization of olefins such as butenes [J.Am.Chem.Soc., 82, 387 (1960)].

Catalyst B may be prepared by dispersing the alkali metal into a liquid medium such as toluene, xylene or mineral oil. The suitable dispersing medium is inactive for the alkali metal and has a boiling point higher than the melting point of the alkali metal. For preparation of a suitable catalyst, the alkali metal is dispersed into the liquid medium at a temperature higher than the melting point of the alkali metal with stirring. The amount of the alkali metal to be dispersed is usually from 20 to 60% by weight based on the combined weight of the alkali metal and the liquid medium.

Catalyst C is an alkali metal alloy which is liquid at the process conditions, such as sodium-potassium alloy. In case of sodium-potassium alloy, for instance, the alloy containing 22 to 95% by weight of potassium has a melting point lower than 50°C and the alloy containing 77% by weight of potassium has a melting point of −12°C. The racemization proceeds very easily by stirring the reaction mixture when the alkali metal alloy mentioned above is used as a catalyst in the reaction temperature range of from about −10° to 50°C.

The optically active amine to which this invention is applicable is the one represented by the formula [I] wherein $R_1$ is preferably alkyl having not more than 8 carbon atoms (e.g. methyl, ethyl, propyl, isopropyl, butyl, sec.- butyl, t-butyl, cyclohexyl, cyclohexylmethyl), aralkyl (e.g. benzyl, phenethyl, naphthylmethyl, naphthylethyl) or aryl having not more than 18 carbon atoms (e.g. phenyl, naphthyl) and $R_2$ is favorably aryl having not more than 18 carbon atoms (e.g. phenyl, naphthyl) or alkoxycarbonyl having not more than 9 carbon atoms (e.g. methoxycarbonyl, ethoxycarbonyl, propoxycarbonyl, isopropoxycarbonyl, butoxycarbonyl, sec.- butoxycarbonyl, t-butoxycarbonyl, cyclohexyloxycarbonyl). Among the said significances of the symbols $R_1$ and $R_2$, the aryl or aralkyl moiety may bear one or more alkyl or alkoxy groups of not more than 4 carbon atoms on the aromatic ring. Specific examples of the optically active amine [I] are α-phenylethylamine, α-phenylpropylamine, α-(p-tolyl)ethylamine, α-(1- or 2-naphthyl)ethylamine, α,β-diphenylethylamine, β-(p-, o- or m-tolyl)-α-phenylethylamine, β-(p-, o- or m-ethylphenyl)-α-phenylethylamine, β-[p-, o- or m-(n- or i-)-propylphenyl]-α-phenylethylamine, β -[p-, o- or m-(n-, i- or t-)-butylphenyl]-α-phenylethylamine, β-phenyl-α-(p-, o- or m-tolyl)ethylamine, β-phenyl-α-(p-, o- or m-ethylphenyl- )ethylamine, β-phenyl-α-[p-, o- or m-(n- or i-)-propylphenyl]ethylamine, β-phenyl-α-[p-, o- or m-(n-, i- or t-)-butylphenyl]ethylamine, β-(p-, o- or m-tolyl)-α-(p-, o- or m-tolyl)ethylamine, β-(p-, o- or m-tolyl)-α-(p-, o- or m-ethylphenyl)ethylamine, β-(p-, o- or m-tolyl)-α-[p-, o- or m-(n- or i-)-propylphenyl]ethylamine, β-(p-, o- or m-tolyl)-α-[p-, o- or m-(n-, i- or t-)-butylphenyl]ethylamine, β-(p-, o- or m-ethylphenyl)-α-(p-, o- or m-ethylphenyl)ethylamine, β-(p-, o- or m-ethylphenyl)-α-(p-, o- or m-tolyl)ethylamine, β-(p-, o- or m-ethylphenyl)-α-[p-, o- or m-(n- or i-)-propylphenyl]ethylamine, β-(p-, o- or m-ethylphenyl)-α-[p-, o- or m-(n-, i- or t-)-butylphenyl]ethylamine, β-[p-, o- or m-(n- or i-)-propylphenyl]-α-(p-, o- or m-tolyl)ethylamine, β-[p-, o- or m-(n- or i-)propylphenyl]-α-(p-, o- or m-ethylphenyl)ethylamine, β-[(p-, o- or m-(n- or i-)-propylphenyl]-α-[p-, o- or m-(n- or i-)propylphenyl]ethylamine, β-[p-, o- or m-(n- or i-)-propylphenyl]-α-[p-, o- or m-(n-, i- or t-)-butylphenyl]ethylamine, β-[p-, o- or m-(n-, i- or t-)-butylphenyl]-α-(p-, o- or m-tolyl)ethylamine, β-[p-, o- or m-(n-, i- or t-)-butylphenyl]-β-(p-, o- or m-ethylphenyl)ethylamine, β-[p-, o- or m-(n-, i- or t-)-butylphenyl]-α-[p-, o- or m-(n- or i-)propylphenyl]ethylamine, β-[p-, o- or m-(n-, i- or t-)butylphenyl]-α-[p-, o- or m-(n-, i- or t-)-butylphenyl]ethylamine, alanine methyl ester, alanine butyl ester, norvaline propyl ester, leucine ethyl ester, β-cyclohexylalanine methyl ester, β-phenylalanine methyl ester, β-phenylalanine propyl ester, β-3,4-dimethoxyphenylalanine ethyl ester, etc.

The optically active amine [I] may include the d-form and/or l-form in any proportion.

The racemization may be performed batchwise or continuously. The optically active amine [I] may be introduced alone or together with the catalyst into a reactor wherein the racemization is effected. When desired, it may be introduced into the reactor successively or intermittently depending on the proceeding of the racemization.

The proportion of the catalyst to the optically active amine [I] does not have to be controlled strictly. Thus, the catalyst may be used in such an amount that an appropriate yield of the racemic mixture is obtained within a proper reaction time. From the economical point of view, however, the catalyst is usually employed in an amount of about 1/1000 to 1/5 mole, preferably of about 1/200 to 1/10 mole, to 1 mole of the said optically active amine [I].

The reaction temperature in the present method should be set in the range of about −10° to 50°C for the successful accomplishment of the racemization. When the reaction temperature is lower than about −10°C, the rate of racemization is too slow for the industrial purpose. When higher than about 50°C, the rate of racemization is faster but the decomposition of the optically active amine [I] and/or any other unfavorable side reaction takes place.

The racemization can proceed quantitatively even if any solvent is not present. If desired, there may be used any solvent which does not afford any unfavorable influence on the proceeding of the racemization. In order to accomplish the racemization assuredly, the operation may be carried out under the atmosphere of any inert gas. Further, the elimination of any water or moisture from the optically active amine [I] prior to the contact with the catalyst is ordinarily favored.

The reaction time is more or less associated with the amount of the catalyst and the reaction temperature. It is usually more shortened with a larger amount of the catalyst and a higher reaction temperature.

The proceeding of the racemization can be traced, for instance, by measuring the optical rotation at a certain concentration or by analyzing with gas-chromatography.

After completion of the reaction, the recovery of the product may be carried out by a conventional purification procedure. For instance, the reaction mixture is, after elimination of the catalyst therefrom, treated by distillation or chromatography. The purification may be also carried out with the formation of the salt of the resultant amine [I] with an acid. Since the racemization proceeds quantitatively, the reaction product may be of high purity, even if any purification procedure is not applied.

By the method of this invention, racemization can be carried out quantitatively using a small amount of the catalyst under a mild condition. Accordingly, it is quite convenient from the viewpoints of operation, apparatus and economy.

Practical and presently preferred embodiments of this invention are illustratively shown in the following Examples.

Part I

Under this Part, the examples of the racemization by the use of Catalyst A are shown. The catalysts as used were prepared as follows:

Procedure A

In a 200 ml flask, alumina of 200 to 300 mesh in particle size (100 g) calcined at 500°C for 2 hours was charged and heated at 400°C under a nitrogen atmosphere while stirring. After the addition of metallic sodium (10 g) at the same temperature as above, the resultant mixture was stirred for one hour to give a catalyst (i.e. an alkali metal deposited on a solid carrier).

Procedure B

As in Procedure A, there was prepared a catalyst from alumina (100 g) and metallic potassium (6 g) by heating at 200°C.

Procedure C

As in Procedure A, there was prepared a catalyst from alumina (100 g) and metallic potassium (5 g) by heating at 200°C.

EXAMPLE 1

In a 50 ml flask, 25 g of (+)-α-(1-naphthyl)ethylamine ($[\alpha]_D^{20}$ +81.3° (neat)) was charged under nitrogen, and the catalyst prepared as in Procedure A (5.0 g) was added thereto. The resulting mixture was stirred at room temperature. The optical rotation of the reaction mixture measured with elapse of the reaction time was as shown in Table 1.

Table 1

| Reaction time (hrs.) | $[\alpha]_{578}^{20}$ (c 1, ethanol) |
|---|---|
| 0 | +57.1° |
| 1 | +30.4° |
| 2 | +13.2° |
| 3 | +4.6° |
| 5 | +1.9° |

The catalyst was filtered off and washed with toluene, and the filtrate was concentrated and then distilled under reduced pressure to give racemic α-(1-naphthyl)ethylamine (22.4 g). B.P. 124° to 126°C/2.0 mmHg. $n_D^{20}$ 1.6224.

EXAMPLE 2

In a 100 ml reactor, 20 g of (−)-α-(1-naphthyl)ethylamine ($[\alpha]_D^{20}$ −58.2° (neat)) and 30 g of dry toluene were charged under nitrogen, and the catalyst prepared as in Procedure B (4.0 g) was added thereto. The mixture was stirred at 30°C for 4 hours. After filtering off the catalyst, the filtrate was treated as in Example 1 to give 17.3 g of racemic α-(1-naphthyl)ethylamine. B.P. 102° to 105°C/0.3 mmHg. $[\alpha]_D^{25}$ −0.7° (neat).

EXAMPLE 3

In a 100 ml flask, 50 g of (+)-α-phenyl-n-propylamine ($[\alpha]_D^{25}$ +21.0° (neat)) was charged under nitrogen, and the catalyst prepared as in Procedure A (3.0 g) was added thereto. The mixture was stirred at 25°C for 7 hours. After filtering off the catalyst, the filtrate was distilled under reduced pressure to give 46.3 g of racemic α-phenyl-n-propylamine. B.P. 99° to 100°C/16 mmHg. $[\alpha]_D^{25}$ +0.1° (neat).

EXAMPLE 4

In a 100 ml flask, 50 g of (−)-α-(p-tolyl)ethylamine ($[\alpha]_D^{25}$ −34.0° (neat)) was charged under nitrogen, and the catalyst prepared as in Procedure B (3.0 g) was added thereto. The resultant mixture was stirred at 30°C for 5 hours. After filtering off the catalyst, the filtrate was distilled under reduced pressure to give 43.9 g of racemic α-(p-tolyl)ethylamine. B.P. 100° to 102°C/17 mmHg. $[\alpha]_D^{25}$ −0.3° (neat).

EXAMPLE 5

In a 50 ml flask, 20.0 g of (−)-α-phenyl-β-(p-tolyl)ethylamine ($[\alpha]_D^{25}$ −12.5° (neat)) was charged under nitrogen, and the catalyst prepared as in Procedure A (3.5 g) was added thereto. The mixture was stirred at 20°C. The optical rotation of the reaction mixture measured with elapse of the reaction time was as shown in Table 2.

Table 2

| Reaction time (hrs.) | $[\alpha]_D^{25}$ (neat) |
|---|---|
| 0 | −12.5° |
| 1 | −10.9° |
| 2 | −5.8° |
| 3 | −2.6° |
| 5 | −1.2° |
| 7 | −0.6° |

After filtering off the catalyst, the filtrate was distilled under reduced pressure to give racemic α-phenyl-β-(p-tolyl)ethylamine (16.0 g). B.P. 132° to 133°C/1.5 mmHg. $n_D^{25}$ 1.5668.

EXAMPLE 6

In a 100 ml flask, 20 g of (−)-α-phenyl-β-(p-tolyl)ethylamine ($[\alpha]_D^{25}$ −8.5° (neat)) and 30 g of dry toluene were charged under nitrogen, and the catalyst prepared as in Procedure C (4.0 g) was added thereto. The mixture was stirred at 20°C for 7 hours. After filtering off the catalyst, toluene was distilled off from the filtrate, and the residue was distilled under reduced pressure to give 17.5 g of racemic α-phenyl-β-(p-tolyl)ethylamine. B.P. 120° to 124°C/0.2 mmHg. $[\alpha]_D^{25}$ −0.3° (neat).

EXAMPLE 7

In a 50 ml flask, 50 g of L-β-phenylalanine methyl ester ($[\alpha]_D^{25}$ +22.3° (neat)) was charged under nitrogen, and the catalyst prepared as in Procedure A (3.7 g) was added thereto. The mixture was stirred at 25°C. The optical rotation of the reaction mixture measured with elapse of the reaction time was shown in Table 3.

Table 3

| Reaction time (min.) | $[\alpha]_D^{25}$ (c 1, ethanol) |
|---|---|
| 0 | +27.6° |
| 30 | +22.3° |
| 60 | +16.1° |
| 120 | +8.3° |
| 160 | +3.5° |
| 240 | +0.3° |

After filtering off the catalyst, the filtrate was distilled to give 42.5 g of racemic β-phenylalanine methyl ester. B.P. 90° to 92°C/0.3 mmHg. $[\alpha]_D^{25}$ +0.2° (neat).

EXAMPLE 8

In a 25 ml flask, 12.0 g of L-leucine ethyl ester was charged under nitrogen, and the catalyst prepared as in Procedure B (1.8 g) was added thereto. The mixture was stirred at 20°C for 5 hours. After filtering off the catalyst, the filtrate was distilled under reduced pressure to give 10.3 g of racemic leucine ethyl ester. B.P. 83° to 84°C/12 mmHg. $[\alpha]_D^{20}$ +0.3° (neat).

EXAMPLE 9

In a 25 ml flask, 10 g of L-diethyl aspartate ($[\alpha]_D^{25}$ −9.5° (neat)) was charged under nitrogen, and the catalyst prepared as in Procedure A (1.7 g) was added thereto. The mixture was stirred at 25°C for 3 hours. After filtering off the catalyst, the filtrate was distilled under reduced pressure to give 9.0 g of racemic diethyl aspartate. B.P. 85° to 86°C/1.0 mmHg. $[\alpha]_D^{25}$ −0.4° (neat).

EXAMPLE 10

In a 100 ml flask, 20 g of L-β-phenylalanine methyl ester ($[\alpha]_D^{25}$ +22.3° (neat)) and 20 g of dry toluene were charged under nitrogen, and the catalyst prepared as in Procedure A (2.0 g) was added thereto. The mixture was stirred at 30°C for 5 hours. After filtering off the catalyst, toluene was distilled off, and the residual solution was distilled under reduced pressure to give 17.0 g of racemic β-phenylalanine methyl ester. B.P. 90° to 92°C/0.3 mmHg. $[\alpha]_D^{25}$ +0.3° (neat).

Part II

Under this Part, the examples of the racemization by the use of Catalyst B are shown.

EXAMPLE 11

In a 25 ml flask, 10 g of (−)-α-phenylethylamine ($[\alpha]_D^{20}$ −39° (neat)) was charged under nitrogen, and 40% sodium dispersion in liquid paraffin (0.2 g) was added thereto. The mixture was stirred at 25°C for 5 hours. Then, a small amount of ethanol was added to the reaction mixture, whereby the catalyst was inactivated. After the addition of water, the resultant mixture was extracted with toluene. The toluene extract was concentrated and distilled under reduced pressure to give 8.8 g of racemic α-phenylethylamine. B.P. 105° to 107°C/53 mmHg. $[\alpha]_D^{25}$ −0.2° (neat). $n_D^{20}$ 1.5253.

EXAMPLE 12

In a 25 ml flask, 10 g of L-alanine ethyl ester ($[\alpha]_D^{20}$ −2.3° (neat)) was charged under nitrogen, and 40% sodium dispersion in liquid paraffin (0.15 g) was added thereto. The mixture was stirred at 27°C for 3 hours. Then, the reaction mixture was treated as in Example 11 to give 8.7 g of racemic alanine ethyl ester. B.P. 48° to 52°C/20 mmHg. $[\alpha]_D^{20}$ 0° (neat).

EXAMPLE 13

In a 25 ml flask, 10 g of (−)-β-phenyl-α-(p-tolyl)ethylamine ($[\alpha]_D^{25}$ −8.7° (neat)) was charged under nitrogen, and 40% sodium dispersion in liquid paraffin (0.2 g) was added thereto. The mixture was stirred at 35°C for 6 hours. Then, the reaction mixture was treated as in Example 11 to give 9.2 g of racemic β-phenyl-α-(p-tolyl)ethylamine. B.P. 107° to 109°C/0.07 mmHg. $[\alpha]_D^{25}$ −0.1° (neat). $n_D^{25}$ 1.5711.

Part III

Under this Part, the examples of the racemization by the use of Catalyst C are shown.

EXAMPLE 14

In a 25 ml flask, 10 g of (+)-α-(1-naphthyl)ethylamine ($[\alpha]_D^{20}$ +81.3° (neat)) was charged under nitrogen, and sodium-potassium alloy (Na : K = 56 : 44 by weight) (0.1 g) was added thereto. The mixture was stirred at 20°C for 3 hours. The reaction mixture was treated as in Example 11 to give 9.3 g of racemic α-(1-naphthyl)ethylamine. B.P. 124° to 126°C/2.0 mmHg. $[\alpha]_D^{25}$ −0.2° (neat).

EXAMPLE 15

In a 25 ml flask, 10 g of (+)-α,β-diphenylethylamine ($[\alpha]_D^{25}$ +13.4° (neat)) was charged under nitrogen, and sodium-potassium alloy (Na : k = 56 : 44 by weight) (0.1 g) was added thereto. The mixture was stirred at 25°C for 2 hours. The reaction mixture was treated as in Example 11 to give 9.5 g of racemic α,β-diphenylethylamine. B.P. 114° to 116°C/0.3 mmHg. $[\alpha]_D^{25}$ +0.1° (neat). $n_D^{25}$ 1.5770.

EXAMPLE 16

In a 100 ml flask, 50 g of (+)-α-phenyl-β-(p-tolyl)ethylamine ($[\alpha]_D^{25}$ +12.5° (neat)) was charged under nitrogen, and sodium-potassium alloy (Na : k = 56 : 44 by weight) (0.2 g) was added thereto. The resulting mixture was stirred at 25°C for 5 hours. The reaction mixture was treated as in Example 11 to give 46.9 g of racemic α-phenylβ-(p-tolyl)ethylamine. B.P. 121° to 124°C/0.2 mmHg. $[\alpha]_D^{25}$ +0.2° (neat).

EXAMPLE 17

In a 25 ml flask, 13.0 g of D-β-phenylalanine ethyl ester was charged under nitrogen, and sodium-potassium alloy (Na : K = 56 : 44 by weight) (0.1 g) was added thereto. The mixture was stirred at 20°C for 3 hours. The reaction mixture was treated as in Example 11 to give 12.1 g of racemic β-phenylalanine ethyl ester. B.P. 95° to 96°C/0.6 mmHg. $[\alpha]_D^{25}$ −0.1° (neat).

What is claimed is:

1. A method for racemization of optically active amines which comprises contacting an optically active amine of the formula:

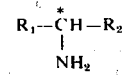

wherein C* is an asymmetric carbon atom, $R_1$ is alkyl, aralkyl or aryl C. $R_2$ is aryl or alkoxycarbonyl, the aryl or aralkyl moiety being unsubstituted or being substituted with one or more alkyl or alkoxy groups on the aromatic ring, provided that $R_1$ and $R_2$ are always different from each other, with an alkali metal catalyst selected from the group consisting of (1) an alkali metal deposited on a solid carrier, (2) an alkali metal dispersed in a liquid medium and (3) an alkali metal alloy at a temperature of from −10° to 50°C 2. The method according to claim 1, wherein $R_1$ is aralkyl and $R_2$ is aryl.

3. The method according to claim 1, wherein $R_1$ is alkyl and $R_2$ is aryl.

4. The method according to claim 1, wherein $R_2$ is alkoxycarbonyl.

5. The method according to claim 1, wherein the catalyst is used in an amount of about 1/1000 to 1/5 mole per 1 mole of the optically active amine.

6. The method according to claim 1, wherein the catalyst is used in an amount of about 1/200 to 1/10 mole per 1 mole of the optically active amine.

7. The method according to claim 1, wherein $R_1$ is an alkyl group having not more than 8 carbon atoms or an aryl group having not more than 18 carbon atoms and $R_2$ is an aryl group having not more than 18 carbon atoms or an alkoxycarbonyl group having not more than 9 carbon atoms.

8. The method according to claim 1, wherein the aryl or aralkyl moieties are substituted with one or more alkyl or alkoxy groups having not more than 4 carbon atoms on the aromatic ring.

9. The method according to claim 1, wherein the optically active amine is α-phenylethylamine, α,β-diphenylethylamine, α-phenyl-β-(p-tolyl)ethylamine, β-phenyl-α-(p-tolyl)ethylamine or α-naphthylethylamine.

* * * * *